US010835765B2

(12) United States Patent
Tulik et al.

(10) Patent No.: US 10,835,765 B2
(45) Date of Patent: Nov. 17, 2020

(54) DETERMINATION OF GEOMETRICAL INFORMATION ABOUT A MEDICAL TREATMENT ARRANGEMENT COMPRISING A ROTATABLE TREATMENT RADIATION SOURCE UNIT

(71) Applicant: OptiNav Sp. z o.o., Slupsk (PL)

(72) Inventors: Monika Tulik, Warsaw (PL); Damian Kabat, Cracow (PL); Radoslaw Kycia, Sieniawa (PL); Zbigniew Latala, Cracow (PL); Zbislaw Tabor, Wieliczka (PL)

(73) Assignee: OptiNav SP. z o.o., Slupsk (PL)

( * ) Notice: Subject to any disclaimer, the term of this patent is extended or adjusted under 35 U.S.C. 154(b) by 111 days.

(21) Appl. No.: 16/022,356

(22) Filed: Jun. 28, 2018

(65) Prior Publication Data

US 2019/0001156 A1    Jan. 3, 2019

(30) Foreign Application Priority Data

Jun. 28, 2017  (EP) .................................... 17178405

(51) Int. Cl.
  *A61N 5/10*    (2006.01)
  *A61B 6/00*    (2006.01)
(52) U.S. Cl.
  CPC ............. *A61N 5/1075* (2013.01); *A61B 6/58* (2013.01); *A61B 6/582* (2013.01); *A61B 6/583* (2013.01);
  (Continued)
(58) Field of Classification Search
  CPC ......... A61B 6/582; A61B 6/583; A61B 6/584; A61B 6/58; A61N 5/1048; A61N 5/1075;
  (Continued)

(56) References Cited

U.S. PATENT DOCUMENTS

| | | | | |
|---|---|---|---|---|
| 5,034,969 A | * | 7/1991 | Ozaki | A61B 6/583 378/162 |
| 5,442,674 A | * | 8/1995 | Picard | A61B 6/583 378/18 |

(Continued)

FOREIGN PATENT DOCUMENTS

EP    2450083 A1    5/2012

OTHER PUBLICATIONS

W. Mao et al., "Development of a QA phantom and automated analysis tool for geometric quality assurance of on-board MV and kV X-ray imaging systems," Med. Phys. 35, 1497-1506 (2008).

*Primary Examiner* — Allen C. Ho
(74) *Attorney, Agent, or Firm* — Falk Ewers; Ewers IP Law PLLC

(57) ABSTRACT

A method for determining geometrical information about a medical treatment arrangement that includes a rotatable treatment radiation source unit is provided. The method includes attaching a phantom to a patient support of the medical treatment arrangement, attaching a calibration module to the rotatable treatment radiation source unit to permit the calibration module to rotate together with the rotatable treatment radiation source unit when the rotatable treatment radiation source unit is rotated, obtaining for each of a plurality of rotational positions of the rotatable treatment radiation source unit a projection image of the phantom and of the calibration module by an image detector, while a part of the calibration module is positioned in a radiation propagation zone between the rotatable treatment radiation source unit and the image detector, evaluating the images, obtaining an evaluation result, and determining geometrical information about the medical treatment arrangement from the evaluation result.

16 Claims, 7 Drawing Sheets

(52) U.S. Cl.
CPC .............. *A61B 6/584* (2013.01); *A61N 5/10* (2013.01); *A61N 5/1039* (2013.01); *A61N 5/1048* (2013.01); *A61N 5/1081* (2013.01); *A61N 5/1082* (2013.01); *A61N 2005/1076* (2013.01); *A61N 2005/1097* (2013.01)

(58) Field of Classification Search
CPC .............. A61N 2005/1076; A61N 5/10; A61N 5/1081; A61N 5/1082
USPC .................................................. 378/65, 207
See application file for complete search history.

(56) References Cited

U.S. PATENT DOCUMENTS

| | | | | |
|---|---|---|---|---|
| 5,963,612 A * | | 10/1999 | Navab | A61B 6/4441 378/17 |
| 5,964,715 A * | | 10/1999 | Thunberg | A61B 90/36 378/207 |
| 6,379,043 B1 * | | 4/2002 | Zylka | A61B 6/547 378/207 |
| 6,382,835 B2 * | | 5/2002 | Graumann | A61B 6/4405 378/196 |
| 6,466,638 B1 * | | 10/2002 | Silver | G06T 11/006 378/4 |
| 6,490,477 B1 * | | 12/2002 | Zylka | A61B 6/04 600/414 |
| 6,491,430 B1 * | | 12/2002 | Seissler | H04N 5/32 378/207 |
| 6,535,574 B1 * | | 3/2003 | Collins | A61N 5/1049 378/20 |
| 6,715,918 B2 * | | 4/2004 | Mitschke | A61B 6/583 378/163 |
| 6,851,855 B2 * | | 2/2005 | Mitschke | A61B 6/547 378/205 |
| 6,865,253 B2 * | | 3/2005 | Blumhofer | A61B 6/547 378/205 |
| 6,888,924 B2 * | | 5/2005 | Claus | A61B 6/583 378/163 |
| 6,912,265 B2 * | | 6/2005 | Hebecker | G06T 11/003 378/15 |
| 6,932,506 B2 * | | 8/2005 | Mitschke | A61B 6/584 250/252.1 |
| 7,016,456 B2 * | | 3/2006 | Basu | A61B 6/032 378/18 |
| 7,050,531 B2 * | | 5/2006 | Hebecker | G06T 11/006 378/4 |
| 7,147,373 B2 * | | 12/2006 | Cho | A61B 6/547 378/207 |
| 7,186,023 B2 * | | 3/2007 | Morita | A61B 6/466 378/18 |
| 7,594,753 B2 * | | 9/2009 | Main | A61N 5/1048 378/207 |
| 7,640,607 B2 * | | 1/2010 | Guertin | A61B 6/547 5/601 |
| 7,780,351 B2 * | | 8/2010 | Heigl | A61B 6/032 378/207 |
| 7,950,849 B2 * | | 5/2011 | Claus | G06T 11/005 378/18 |
| 7,961,927 B2 * | | 6/2011 | Gagnon | G06T 3/4061 382/131 |
| 8,007,173 B2 * | | 8/2011 | Paidi | A61B 6/584 378/207 |
| 8,104,958 B2 * | | 1/2012 | Weiser | A61B 6/583 378/162 |
| 8,180,130 B2 * | | 5/2012 | Sebok | G06T 7/74 378/20 |
| 8,220,994 B2 * | | 7/2012 | Heigl | A61B 6/547 378/207 |
| 8,363,919 B2 * | | 1/2013 | Sebok | G06K 9/3216 382/131 |
| 8,379,794 B2 * | | 2/2013 | Poulsen | A61B 6/583 378/65 |
| 8,391,580 B2 * | | 3/2013 | Bornfleth | G06T 7/251 382/132 |
| 8,417,318 B2 * | | 4/2013 | West | A61B 34/20 600/424 |
| 8,488,862 B2 * | | 7/2013 | Bose | A61N 5/1075 378/132 |
| 8,768,026 B2 * | | 7/2014 | Ren | A61B 6/0414 382/131 |
| 8,804,912 B2 * | | 8/2014 | Akahori | A61B 6/583 378/163 |
| 8,845,191 B2 * | | 9/2014 | Ngar | G05B 19/4015 378/207 |
| 8,891,849 B2 * | | 11/2014 | Rohler | A61B 6/032 382/132 |
| 9,044,190 B2 * | | 6/2015 | Rubner | A61B 6/4405 |
| 9,259,192 B2 * | | 2/2016 | Ishihara | A61B 6/032 |
| 9,323,896 B2 * | | 4/2016 | Fält | G16B 50/00 |
| 9,408,579 B2 * | | 8/2016 | Yamakawa | A61B 6/14 |
| 9,435,895 B2 * | | 9/2016 | Ruschin | G01T 7/005 |
| 9,526,471 B2 * | | 12/2016 | Goodenough | A61B 6/025 |
| 9,610,056 B2 * | | 4/2017 | Lavallee | A61B 6/032 |
| 9,613,438 B2 * | | 4/2017 | Takemoto | A61B 6/5264 |
| 9,616,251 B2 * | | 4/2017 | Filiberti | A61N 5/1048 |
| 9,643,029 B2 * | | 5/2017 | Scheib | A61N 5/1049 |
| 9,672,607 B2 * | | 6/2017 | Demri | A61B 5/064 |
| 9,681,851 B2 * | | 6/2017 | Rohler | A61B 6/032 |
| 9,693,749 B2 * | | 7/2017 | Ni | G01N 23/046 |
| 9,844,685 B2 * | | 12/2017 | Suzuki | A61N 5/1049 |
| 9,888,902 B2 * | | 2/2018 | Ueki | A61B 6/032 |
| 9,962,561 B2 * | | 5/2018 | Meir | G06T 7/85 |
| 9,990,863 B2 * | | 6/2018 | Chiribiri | A61B 6/583 |
| 10,022,104 B2 * | | 7/2018 | Sell | A61B 6/584 |
| 10,105,119 B2 * | | 10/2018 | Marcelis | A61B 6/4014 |
| 10,111,625 B2 * | | 10/2018 | Toba | A61B 6/582 |
| 10,119,922 B2 * | | 11/2018 | Bernard | A61B 6/032 |
| 10,169,845 B2 * | | 1/2019 | Sakaguchi | A61B 6/5258 |
| 10,180,483 B2 * | | 1/2019 | Holdsworth | G01R 33/58 |
| 10,183,177 B2 * | | 1/2019 | Meir | A61N 5/1081 |
| 10,203,395 B2 * | | 2/2019 | Foxall | A61B 6/583 |
| 10,286,230 B2 * | | 5/2019 | Berke | A61N 5/1075 |
| 10,327,731 B2 * | | 6/2019 | Hong | A61B 6/037 |
| 10,383,202 B2 * | | 8/2019 | Canfield | H05G 1/52 |
| 10,383,203 B2 * | | 8/2019 | Meiler | H01J 35/14 |
| 10,395,560 B2 * | | 8/2019 | Groenewald | A61B 6/502 |
| 10,458,926 B2 * | | 10/2019 | Van Stevendaal | G01N 23/04 |
| 10,478,147 B2 * | | 11/2019 | Hawker | A61B 6/032 |
| 10,492,755 B2 * | | 12/2019 | Lin | A61B 6/461 |
| 10,499,875 B2 * | | 12/2019 | Fieselmann | A61B 6/54 |
| 10,507,003 B2 * | | 12/2019 | Uber, III | A61B 6/5288 |
| 10,507,004 B2 * | | 12/2019 | Daerr | A61B 6/5205 |
| 10,507,005 B2 * | | 12/2019 | Jin | A61B 6/482 |
| 10,517,561 B2 * | | 12/2019 | Lin | A61B 6/547 |
| 10,555,715 B2 * | | 2/2020 | Mallozzi | A61B 6/583 |
| 10,569,105 B2 * | | 2/2020 | Kilby | A61N 5/1065 |
| 10,660,600 B2 * | | 5/2020 | Avila | A61B 6/037 |

* cited by examiner

DETERMINATION OF GEOMETRICAL INFORMATION ABOUT A MEDICAL TREATMENT ARRANGEMENT COMPRISING A ROTATABLE TREATMENT RADIATION SOURCE UNIT

CROSS REFERENCE TO RELATED APPLICATIONS

This application claims priority from European patent application EP 17 178 405.1, filed Jun. 28, 2017, the entire content of which is incorporated herein by reference.

TECHNICAL FIELD

The invention relates to the determination of geometrical information about a medical treatment arrangement including a rotatable treatment radiation source unit. In particular, the invention relates to a method of determining the geometrical information and to a medical treatment arrangement.

BACKGROUND

Medical treatment arrangements including a rotatable treatment radiation source unit are known. For example, gantry type arrangements are known (for example as disclosed by EP 2 450 083 A1) which include a radiation source unit attached to a rotatable gantry, a patient support (such as a patient table) and an image detector which can be used for calibration purposes. During tests or calibration, which include the determination of geometrical information about the arrangement, the radiation source unit emits radiation in the direction of a phantom attached to the patient support and an image is obtained using the image detector, which image detector receives radiation from the radiation source unit that has passed through the phantom.

One of the basic assumptions of external beam therapy (EBT), i.e., radiation treatment, is a precise dose delivery to the selected location. This requirement will be met if the geometry of the radiation beam corresponds to the geometry defined in the treatment planning system.

Due to inaccuracies in the construction and due to weights of linear accelerator (linac) components, the actual position of each of the moving elements of an accelerator may differ slightly from the position according to the ideal constructional data, such as CAD (computer aided design) data. These effects are one reason for performing a detailed inspection of work of each of the movable elements of a linac as a part of quality assurance procedures in radiotherapy departments. Also, the position and performance of additional elements like imaging devices of the arrangement may cause inaccuracies. The quality assurance procedures for medical treatment arrangements of the kind mentioned above can be divided with respect to different aspects like dosimetry, mechanics, imaging, operation and general safety. The invention is related at least to dosimetry, mechanics, imaging and operation of a radiation treatment arrangement.

Geometric check and/or calibration procedures include the determination of isocenter positions, in particular the mechanical isocenter of the mechanical system of the radiation source unit, of the mechanical support and motion system for moving the radiation source unit (in particular the gantry) as well as of the patient support (in particular the patient table). In addition, the radiation isocenter position of the radiation source unit is also of interest, in particular with respect to the image detector. Some medical treatment arrangements have additional devices for image guided operation and these devices may also be rotatable, in particular around the patient support. In this case, the isocenter position of the device or devices is also of interest.

In many cases, the radiation source produces a cone-shaped radiation beam, i.e., radiation propagates within a cone-shaped area. In order to limit the spread of the radiation to a defined spatial angle, the radiation source is often combined with a collimator arrangement (in the following: "the collimator") having a first and a second collimator stage. The first collimator stage may be placed nearer to the radiation source compared to the second collimator stage and the second collimator stage may include radiation opaque jaws. In this case, at least the radiation source and the collimator are parts of the radiation source unit. Typically, the collimator is rotatable relative to the radiation source around a rotation axis defined by the spreading direction of the central axis of the radiation beam.

Due to weight and mechanical inaccuracies, the position of the mechanical isocenter can move in space while the radiation source unit rotates around the patient support. The region in which the mechanical isocenter moves may be similar in shape to a sphere. In addition, the direction of the central axis of the radiation beam can unsteadily move because of aging of bearing mechanisms, miscalibration of collimator jaws, tongue-and-groove effect, misalignment of the radiation source unit rotation axis or of the collimator rotation axis. Also, misadjustment of the radiation source position and beam instability may cause this effect. Similarly, additional devices for image-guided radiation therapy (IGRT) may also be misaligned or misadjusted. Ideally, they revolve around a common point of the arrangement, but there are considerable deviations in reality. There is an acknowledged need for the verification of the compatibility between the radiation isocenter and the mechanical isocenters of one or more than one additional image systems. In any case, the accuracy of the geometric information provided by an IGRT system is limited by its geometric stability as well as its precise position and alignment in relation to the radiation source. In particular, flexing or sagging of the imaging system under its own weight during gantry rotation results in inaccuracies of the positions of the radiation source and/all of the image detector that detects radiation from the radiation source.

An analysis of the stability of all mechanical components of the arrangement with respect to a reference point can be performed according to the method of Winston-Lutz that is mentioned in EP 2 450 083 A1. The method is performed with the use of digital imagers, automatic image processing and a simplified cubic phantom containing one radio-opaque fiducial marker. However, the tools used for performing the method may also introduce uncertainties and inaccuracies, e.g., stemming from a mechanical imprecision of the positions of the marker in the phantom, erroneous positioning of the phantom, assumptions made for performing the method and processing of electronic images obtained. In particular, the method is based on assumptions regarding the isocenter position(s) and these assumptions might be incorrect or imprecise.

SUMMARY

It is an object of the present invention to provide a method of determining geometrical information about a medical treatment arrangement including a rotatable treatment radiation source unit, wherein the geometrical information is determinable without assumptions regarding the position and orientation of the rotation axis or of any of the rotation axes of the arrangement. In particular, not only isocenter position(s), but also other geometrical information are determined from the determined rotation axis/axes and angles. For example, the method is applicable to arrangements having an electronic portal imaging devices (EPID), but also to radiotherapy simulators or IGRT systems like a system with kV cone beam computed tomography (CBCT) imaging. It is a further object to provide a medical treatment arrangement that allows the method to be performed.

According to an aspect of the present invention, not only a phantom is used that is attached to the patient support, but also a calibration module that can be considered as a second phantom module. However, unlike a patient, the calibration module is attached to the radiation source unit while the phantom is attached to the patient support. Therefore, and in order to distinguish between the phantom and the calibration module, the calibration module is considered as a separate module.

Furthermore, images of the arrangement including the phantom and the calibration module are obtained by an image detector of the radiation treatment arrangement for different rotational positions of the radiation source unit relative to the phantom, the images are evaluated and geometrical information about the arrangement and thereby the medical treatment arrangement is determined from the evaluation result.

These images may be obtained for rotational positions with respect to a single rotation axis or with respect to a plurality of rotation axes. Each rotation axis corresponds to a rotational degree of freedom. Therefore, depending on the number of rotational degrees of freedom represented by the obtained images, geometrical information related to the rotational degree(s) of freedom can be determined from the images. Typically, the radiation source unit can be rotated around the patient support. This is the case, for example, when the radiation source unit is attached to a rotatable gantry. A different rotational degree of freedom exists if a part (such as a collimator) of the radiation source unit is rotatable about a central axis of the radiation beam that is generated by the radiation source and shaped by the collimator and if this rotation affects the geometry of the radiation beam. The central axis is in particular an axis that is central with respect to jaws of the collimator, and more specially with respect to the jaws of a secondary stage of the collimator. However, the central axis of the radiation beam might slightly differ from the rotation axis. In many cases, a further rotational degree of freedom is realized by a rotatable patient support (such as a rotatable patient table).

Since there is no difference in the results obtained by driving a rotation of the radiation source unit or by driving a corresponding rotation of the patient support, the term "rotatable radiation source unit" also includes the case that the radiation source unit is fixed in the laboratory coordinate system and only the patient support is rotated. Since the phantom is attached to the patient support and therefore rotates when the patient support is rotated, i.e., the phantom is fixed relative to the patient support, only the relative rotation of the patient support and of the radiation source unit matters. Of course, not only rotational degrees of freedom exist, but also linear (also called "translational") degrees of freedom, i.e., degrees of freedom corresponding to movements along linear straight lines. As mentioned above, real rotational movements differ from ideal rotational movements and often include movement components with respect to at least one linear degree of freedom. Therefore, the images which are obtained for different rotational positions of the patient support and of the radiation source unit also include information about linear degrees of freedom. In other words, it is one purpose to determine also movement components with respect to any linear degree of freedom, since this allows for determining inaccuracies of the rotational movements.

Without assumptions (such as a physical model of the rotation mechanics) concerning the rotational position and the rotation axis/axes of the radiation source unit, its rotation isocenter cannot be determined if only the phantom is attached to the patient support, but if no calibration module is attached to the radiation source unit. Therefore, in order to succeed without the need for such assumptions, the method according to the present invention uses the calibration module.

According to an exemplary embodiment of the calibration module, it includes a set of fiducial markers, in particular at least three fiducial markers. Preferably, at least three of these fiducial markers are visible and/or detectable in each of the images obtained by the image detector. The distances between the fiducial markers (in particular between for each marker one point, e.g., the center point of a spherical marker) and/or other geometrical quantities related to the set of fiducial markers are fixed. Typically, the distances and/or other geometrical quantities are known, for example from precise separate measurements performed on the calibration module. However, since the distances and/or other geometrical quantities are fixed, they remain constant when the rotatable treatment radiation source unit is rotated. Therefore, geometrical information about the medical treatment arrangement can also be obtained for different rotational positions of the radiation source unit relative to the patient support if the distances and/or other geometrical quantities are not known.

In particular, a set of fiducial markers (in particular point markers, such as ball markers, and/or line markers and/or any other kind of fiducial markers) includes features that allow for the determination of the position and orientation of the set of markers—and thereby of the calibration module and of the complete radiation source unit or a part of the radiation source unit—from a number of projection images of the set of markers. Allowing for the determination of the position and orientation means that the set of markers allows for the determination of coordinates with respect to six degrees of freedom, three translational degrees of freedom and three rotational degrees of freedom. For example, such a set of markers may include three point markers, wherein the distances of the three points (e.g., the centers of spherical markers) are known, three line markers the lines of which pairwise intersect each other, wherein the angles of intersection are known, or five point markers, wherein the pairwise distances of the points are unknown, but fixed (i.e., do not change when the arrangement is rotated). However, other arrangements forming the set of fiducial markers are also possible. The required number of projection images depends on the set of fiducial markers that is used. For example, a single projection image is sufficient in case of the set of fiducial markers having three point markers where the pairwise distances of the points is known and fixed. Two projection images are sufficient in case of the set of fiducial markers having five point markers where the pairwise distances are fixed but unknown.

Examples of fiducial markers, the related geometrical quantity or quantities and of the determination of the related geometrical quantity or quantities will be described.

In any case, the phantom and the calibration module enable the arrangement and/or user to unambiguously determine the rotational and translational position of the calibration module and thereby of the radiation source unit relative to the phantom and thereby relative to the patient support in each image obtained by the image detector.

In particular, a method of determining geometrical information about a medical treatment arrangement including a rotatable treatment radiation source unit is provided, wherein the method includes:

attaching a phantom to a patient support of the medical treatment arrangement, attaching a calibration module to the rotatable treatment radiation source unit, so that the calibration module rotates together with the rotatable treatment radiation source unit when the rotatable treatment radiation source unit is rotated, obtaining for each of a plurality of rotational positions of the rotatable treatment radiation source unit at least one projection image of the phantom and of the calibration module by using an image detector of the medical treatment arrangement, while at least a part of the calibration module is positioned in a radiation propagation zone between the rotatable treatment radiation source unit and the image detector, evaluating images obtained for the plurality of rotational positions with respect to coordinates of the calibration module in a coordinate system of the phantom, thereby obtaining an evaluation result and determining geometrical information about the medical treatment arrangement from the evaluation result.

Furthermore, a medical treatment arrangement is provided, wherein the arrangement includes:

a rotatable treatment radiation source unit, a patient support, an image detector, being arranged to receive radiation field, that has been emitted by the radiation source and that has interacted with any object in between the radiation source unit and the image detector, and being configured to produce an image corresponding to the radiation field according to a result of interaction with at least one object, a phantom that is attached to the patient support, a calibration module, wherein the calibration module is attached to the rotatable treatment radiation source unit, so that the calibration module rotates together with the rotatable treatment radiation source unit when the rotatable treatment radiation source unit is rotated.

In particular, the medical treatment arrangement may further include:

an evaluation device that is connected to the image detector and/or that is connected to a data storage including projection images generated by the image detector and that is configured to receive projection images of the phantom and of the calibration module obtained by the image detector for each of a plurality of rotational positions of the rotatable treatment radiation source unit, while at least a part of calibration module is positioned in a radiation propagation zone between the rotatable treatment radiation source unit and the image detector, and that is configured to evaluate the projection images with respect to coordinates of the calibration module in a coordinate system of the phantom, thereby obtaining an evaluation result, and a determination device that is connected to the evaluation device or is part of a common unit with the evaluation device and that is configured to determine geometrical information about the medical treatment arrangement from the evaluation result.

The term "coordinate system of the phantom" includes any coordinate system that is fixed relative to the phantom. The origin of the coordinate system may be located within the phantom, at an edge or a corner of the phantom, or outside of the phantom. Typically, a corner of the phantom defines the origin and optionally edges of the phantom extend on the coordinate axes of the coordinate system.

The radiation source of the radiation source unit may be configured to produce radiation for treatment of a patient who rests on the patient support during operation of the arrangement. Additionally or alternatively, the radiation source may be the radiation source of a system for image guided treatment of a patient. It is also possible that the radiation treatment arrangement includes two different radiation source units. In this case, it is typical that a calibration module it is attached to each of the radiation source units. It is possible that the same calibration module is attached first to a first one of the radiation source units and later to another one of the radiation source units. While a calibration module is attached to a radiation source unit, the method according to an aspect of the present invention can be performed, i.e., geometrical information about the rotational degree(s) of freedom of the radiation source unit can be determined.

As mentioned above, at least a part of the calibration module is positioned between the rotatable treatment radiation source unit and the image detector. Therefore, during operation, a radiation beam emitted by the radiation source unit traverses the part of the calibration module or the calibration module and a corresponding projection image can be produced by the image detector.

The phantom may be any phantom suitable for determining its position and orientation in the images obtained by the image detector. In particular, the phantom may include a plurality of fiducial markers the images of which are visible and/or detectable when evaluating the images. Typically, the phantom includes a plurality of fiducial markers that enable the determination of six points related to the plurality of fiducial markers or the determination of equivalent geometrical results, for example of three points, of three vectors and of their lengths.

Fiducial markers of the calibration module and of the phantom may be realized in any suitable form for determining the position of the fiducial marker in the images obtained by the image detector. A group or set of fiducial markers may be realized by an element or region of the calibration module or phantom. This means that the element or region allows for determining not only a single position of the group of fiducial markers, but also for determining an orientation and/or at least one further position of the group of fiducial markers. According to a first exemplary embodiment, each fiducial marker is configured to determine its position only. For instance, spherical fiducial markers allow for precise determination of the position of the center point of the sphere. According to another exemplary embodiment, which can be combined with the first exemplary embodiment, at least one of the fiducial markers is configured to determine a direction or orientation (i.e., a geometrical quantity that can be described by a mathematical vector). For instance, such a fiducial marker may be a straight line that may be defined by an edge or other structure of the calibration unit. For each pair of straight lines that have different directions and that have at least one common point, the set of fiducial markers defines an angle between the lines as a geometrical quantity that can be used for the determination of geometrical information about the medical treatment arrangement from the evaluation result mentioned above. In particular, it is possible to use a combination of different geometrical quantities, such as at least one point defined by a corresponding fiducial point marker in combination with at least one angle between a pair of fiducial line markers.

Therefore, the term "evaluate the projection images with respect to coordinates of the at least three fiducial markers" covers, but is not limited to, the determination of coordinates of points that are defined by in each case one fiducial marker. Rather, it is additionally or alternatively possible to determine other geometrical quantities related to the set of fiducial markers. In particular, such a geometrical quantity may be described by an angle between two straight lines or by a direction.

According to an exemplary embodiment of the method, the rotational movement of the rotatable treatment radiation source or of a part of the rotatable treatment radiation source (e.g., of the collimator) is determined by evaluating projection images obtained for in each case at least two rotational positions. The rotation angle between two of these rotational positions may be small and the method steps may be repeated for different pairs or groups of rotational positions so that the rotational movement is analyzed based on images obtained for a plurality of pairs or groups of rotational positions. This allows for the determination of the movement of the rotation axis as well for the determination of at least one of the isocenters mentioned above.

The mechanical isocenter is understood as the isocenter with respect to at least two rotation axes of mechanical parts (such as of the gantry and of the patient support) that intersect each other or should intersect each other. If, for example, the rotation axes of the gantry and the patient support intersect each other, the intersection point is the current isocenter. If the rotation axes of the gantry and the patient support pass each other at a distance, the middle point on the distance line of the minimal distance can be defined as the current isocenter, for example. As mentioned earlier, the mechanical isocenter may shift during rotation.

A "radiation axis" can be defined, which is a rotation axis of the collimator of the radiation source unit. In case the radiation source unit includes two or more rotation axes that affect the shape and/or orientation of the radiation beam generated by the radiation source unit, a radiation isocenter can be defined as the intersection point of the plurality of rotation axes in the same manner as for the mechanical isocenter.

In particular, the calibration module may comprise a set of fiducial markers, for example at least three fiducial markers. The at least one projection image of the phantom and of the calibration module for each of the plurality of rotational positions of the rotatable treatment radiation source unit can therefore be obtained by using the image detector of the medical treatment arrangement, while the set of fiducial markers of the calibration module is positioned in the radiation propagation zone between the rotatable treatment radiation source unit and the image detector and the images obtained for the plurality of rotational positions can be evaluated with respect to coordinates of the set of fiducial markers in the coordinate system of the phantom, thereby obtaining the evaluation result. In the following, where it is mentioned that positions with respect to coordinates of the calibration module are evaluated, this includes in particular the evaluation of the positions of the set of fiducial markers.

With respect to the medical treatment arrangement, this corresponds to the following: The evaluation device may be configured to receive the projection images of the phantom and of the calibration module obtained by the image detector for each of the plurality of rotational positions of the rotatable treatment radiation source unit, while the set of fiducial markers of the calibration module is positioned in the radiation propagation zone between the rotatable treatment radiation source unit and the image detector, and the evaluation device may be configured to evaluate the projection images with respect to coordinates of the set of fiducial markers in the coordinate system of the phantom, thereby obtaining the evaluation result.

In particular, at least one projection image of the phantom and of the calibration module is obtained for each of at least a first and a second rotational position of the rotatable treatment radiation source unit by using the image detector, so that at least a first projection image corresponding to the first rotational position and a second projection image corresponding to the second rotational position is obtained. In addition, at least the first projection image and the second projection image are evaluated with respect to coordinates of the calibration module, thereby determining positions of the calibration module in the coordinate system of the phantom for each of the at least first and second rotational position.

With respect to the medical treatment arrangement, the evaluation device may be configured to evaluate at least the first projection image and the second projection image with respect to coordinates of the calibration module and in particular of the set of fiducial markers, thereby determining positions of the calibration module and in particular of the set of fiducial markers in the coordinate system of the phantom for each of the at least first and second rotational position.

Thus, geometrical information about the positions of the calibration module, in particular of the set of fiducial markers, and thereby of the radiation source unit or of the part of the radiation source unit are obtained for each of the at least first and second rotational position. This geometrical information is useful for further analysis of the rotational movement and of any translational movement of the radiation source unit. It should be recalled that an active movement of the patient support relative to the radiation source unit is equivalent to a corresponding active movement of the radiation source unit relative to the patient support. Therefore, the method described here is capable of providing geometrical information in both cases and in mixed cases, i.e., when there is active movement of both the patient table and the radiation source unit. The term "active movement" means that the actively moved device is driven, such as by a motored drive and/or manually.

In particular, an angle of rotation of the rotatable treatment radiation source unit or of a part of the rotatable treatment radiation source unit between the first and the second rotational position, an orientation of a rotation axis around which the rotatable treatment radiation source unit or a part of the rotatable treatment radiation source unit has rotated between the first and the second rotational position, and/or a straight linear shift which the rotatable treatment radiation source unit (2) or a part of the rotatable treatment radiation source unit (2) has performed between the first and the second rotational position can be determined from the positions of the calibration module, and in particular of the set of fiducial markers in the coordinate system of the phantom. The positions have been determined for each of the first and second rotational position.

With respect to the medical treatment arrangement, the determination device may be configured to determine the angle of rotation, the orientation and/or the straight linear shift from the positions of the calibration module and in particular of the set of fiducial markers in the coordinate system of the phantom determined by the evaluation device for each of the first and second rotational position.

In particular, the orientation can be determined for each of a plurality of momentary rotation axes around which the rotatable treatment radiation source unit or a part of the rotatable treatment radiation source unit has rotated. For example, as mentioned before, the orientation of each rotation axis can be determined by evaluating at least a first projection image and at least a second projection image for at least a first and a second rotational position. In other words, the orientation of each rotation axis is determined based on geometrical information obtained for at least a first and a second rotational position, wherein the different orientations are determined based on different sets of projection images. This means that the so-called first and second rotational positions considered for the determination of the different orientations differ. For example, one rotational position and another rotational position are considered for the determination of the orientation of a first rotation axis and the other rotational position and a further rotational position are considered for the determination of the orientation of a second rotation axis.

In particular, an orientation of an average rotation axis of the medical treatment arrangement can be determined from orientations of rotation axes determined for a plurality of rotation axes around which the rotatable treatment radiation source unit or a part of the rotatable treatment radiation source unit has rotated.

According to an aspect of the invention, the orientation of the average rotation axis is determined by minimizing errors of the different orientations with respect to the average rotation axis. In the minimization procedure, the errors with respect to potential average rotation axes can be calculated and the average rotation axis is identified for which the errors are minimal. For example, a least square method can be applied for minimization.

In particular, orientations of at least one rotation axis can be determined for different rotational positions. In addition, positions of an isocenter (such as of the mechanical isocenter and/or the radiation isocenter mentioned above) can be determined from a plurality of rotational positions of a mechanical part (such as the gantry or the patient support) of the medical treatment arrangement. The geometrical information required for the determination of the at least one isocenter can be determined as described before and/or as described in the description of the attached figures.

BRIEF DESCRIPTION OF THE DRAWINGS

The invention will now be described with reference to the drawings wherein.

DESCRIPTION OF EXEMPLARY EMBODIMENTS

As mentioned above, a plurality of modules, namely the phantom and the calibration module, are used for the determination of the geometrical information about the arrangement. This does not exclude the use of at least one further module, such as a module attached to the image detector for determining the image detector position and image scale (in particular the pixel size of the matrix of pixels of the detector). If the pixel size is known in advance, this module need not to be used and can be omitted. The image detector orientation can be determined using the phantom.

In the following, an arrangement is described that includes three modules. However, the module which is attached to the image detector can be omitted in other exemplary embodiments.

Figure 1:
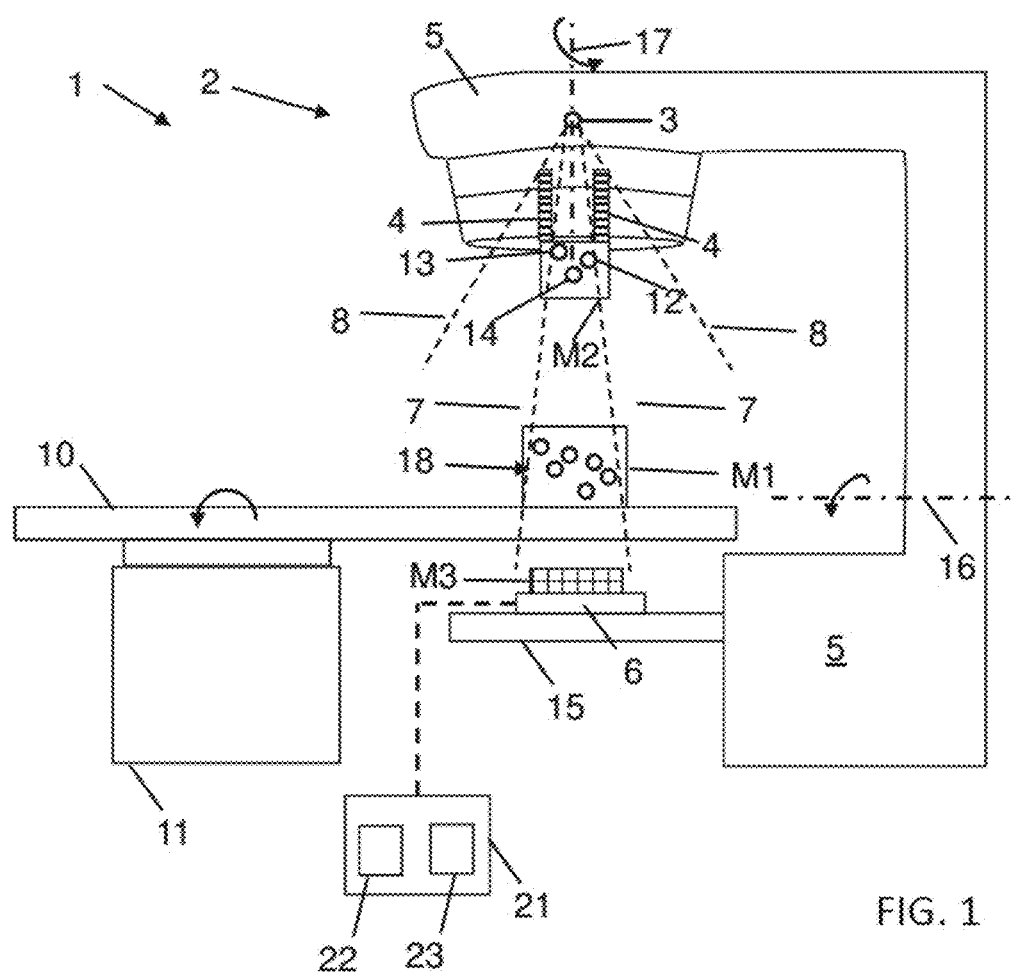
FIG. 1 shows a schematic side view of a radiation treatment arrangement having a gantry, a patient table and an image detector, wherein a module for determining geometric information is attached to each of these three components of the arrangement.

FIG. 1 schematically shows a medical treatment arrangement 1 including a radiation source unit 2, an image detector 6 and a patient support 10 in the form of a patient table. The radiation source unit 2 includes a radiation source 3 and a collimator 4. As indicated by diverging dashed lines 8, the radiation source 3 produces a cone-shaped radiation beam. The collimator 4 shapes and limits the radiation beam that reaches the patient support 10 to a reduced spatial angle, thereby producing a radiation beam that spreads in the example within a pyramidal area having rectangular cross-sections as indicated by dashed lines 7.

The radiation source unit 2 is fixed to a gantry 5. In FIG. 1, an image detector 6 is shown below the patient support 10. The image detector 6 is also fixed to the gantry 5 by a detector support 15. The gantry 5 can be rotated around a first rotation axis 16 that extends in the horizontal direction of FIG. 1. Therefore, the radiation source unit 2 and the image detector 6 can be rotated around the area above the patient support 10 as indicated by a bent arrow. The first rotation axis 16 is not fixed and its position depends on the actual rotational position of the gantry 5.

Furthermore, the radiation source unit 2 can be rotated relative to the gantry 5 (as indicated by a second bent arrow) around a second rotation axis 17 that is coaxial with the central axis of the cone-shaped radiation beam produced by the radiation source unit 2. Patient support 10 rests on a pillar 11 and, as indicated by a third bent arrow, the patient support 10 can be rotated around a third rotation axis that extends perpendicularly to the image plane of FIG. 1. As a result, the surface of the patient support 10 can tilt so that it is no longer horizontally aligned as shown in FIG. 1. Additionally or alternatively, the patient support 10 can be rotated about a fourth rotation axis (not shown) that extends in vertical direction, essentially parallel to the second rotation axis 17.

A computer 21 may be connected to the image detector 6 as indicated by a dashed line in FIG. 1. This connection is understood to be as a virtual connection. In practice, a database may contain the images obtained by the image detector 6 and the computer 21 is connected to the database for evaluation. The computer 21 includes an evaluation device 22 and a determination device 23. The evaluation device 22 is configured to receive images of the phantom M1 and of the calibration module M2 obtained by the image detector 6 for each of a plurality of rotational positions of the rotatable treatment radiation source unit 2, while the at least three fiducial markers 12, 13, and 14 of the calibration module M2 are positioned in a radiation propagation zone between the rotatable treatment radiation source unit 2 and the image detector 6. Furthermore, the evaluation device 22 is configured to evaluate the images with respect to coordinates of the at least three fiducial markers 12, 13, and 14 in a coordinate system of the phantom M1, thereby obtaining an evaluation result. The determination device 23 is part of a common unit (the computer 21) with the evaluation device 22 and is configured to determine geometrical information about the medical treatment arrangement 1 from the evaluation result.

Other exemplary embodiments of the radiation treatment arrangement may differ from the radiation treatment arrangement 1 shown in FIG. 1, in particular with respect to the number and orientation of the rotation axes. Furthermore, at least one additional radiation source unit and an assigned second image detector may be present in such another radiation treatment arrangement, e.g., for image guided therapy and/or examination. The additional radiation source unit may produce (in particular ionizing) invasive radiation that passes through a patient on the patient support 10 and reaches the second image detector in order to provide image information for image guided therapy and/or examination. Additionally or alternatively, the determination device 23 may be connected to a separate evaluation device that is not part of a common unit.

There are three modules M1, M2, and M3 in the radiation treatment arrangement 1 shown in FIG. 1 that are not present when the radiation treatment arrangement 1 is used for treatment of a patient. These three modules are used for determining geometrical information about the radiation treatment arrangement 1. This geometrical information can be used for calibration of the radiation treatment arrangement 1.

The first module is a phantom M1 that is attached to the patient support 10 where a patient would be placed during treatment. As schematically shown in FIG. 1, the phantom M1 includes an arrangement of fiducial markers 18 that includes in the typical example six fiducial markers. According to one exemplary embodiment of the method that will be described in more detail, the coordinates of six points of the set of six fiducial markers are known. This enables the determination of the pairwise distances of the six points. In other words, the mutual positions of the fiducial markers 18 are known. As indicated in FIG. 1, the six fiducial markers 18 may be spheres and the related points may be the center points of the spheres. However, six points may alternatively be defined by another set of fiducial markers 18, for example by a set of three straight lines defining the end points of the straight lines.

The second module is a calibration module M2 rigidly affixed to the radiation source unit 2. For example, a case and/or a support of the collimator 4 may include a standardized mechanical interface (e.g., including guides) for affixing additional equipment to the case and/or a support of the collimator 4. Such additional equipment, for example the calibration module M2, can therefore be attached temporarily to the collimator 4 for (e.g., routinely performed) quality checks. When the projection images intended to be taken for the quality check, in particular for the calibration of the arrangement 1, have been taken, the additional equipment can be removed from the collimator 4. Different additional equipment, such as different kinds of the calibration module, can be provided and each of this additional equipment is shaped and/or there is an adapter that allows for affixing the additional equipment to the mechanical interface, e.g., using the guides mentioned. For example, in order to rigidly fix the calibration module M2 to the radiation source unit 2, the calibration module M2 includes an adapter that fits into these guides. According to an alternative way of temporarily affixing the calibration module to the collimator of the radiation source unit 2, the calibration module M2 is clamped onto the collimator 4, in particular onto the case and/or support, e.g., by inserting projections into corresponding recesses and by continuously loading this connection with a clamping force so that the projections remain in the recesses.

The calibration module M2 includes at least three fiducial markers 12, 13, and 14, which are spherical ball fiducials in the exemplary embodiment. The distances between characteristic points of the at least three fiducial markers 12, 13, and 14 are known. In the exemplary embodiment, the centers of the ball fiducials are the characteristic points.

The third module is a detector module M3 affixed rigidly to the image detector 6. The detector module M3 is used to determine the pixel size of projection images generated by the image detector 6. In the exemplary embodiment, the detector module M3 is a body the shape and size of which is known.

Figure 2:
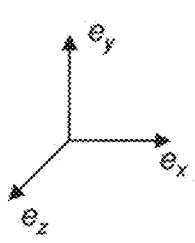
FIG. 2 shows schematically an exemplary embodiment of a phantom in the form of a cube with six spherical fiducial markers.
Figure 2:
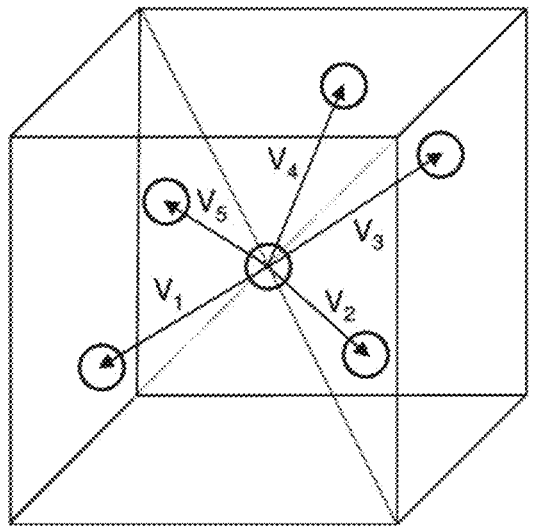

FIG. 2 shows an exemplary embodiment of phantom M1 in the form of a cube. The edges of the cube define a reference coordinate system, i.e., the edges extend in parallel to the coordinate axes $e_x, e_y, e_z$ of the Cartesian coordinate system shown on the left-hand side of FIG. 2. If one of the corners of the cube defines the origin of the coordinate system, the edges starting at the corner extend in line with in each case one of the coordinate axes $e_x, e_y, e_z$. The six fiducial markers of radiation opaque material that are arranged within the cube are spherical fiducials (i.e., ball markers). The material of the cube in which the fiducial markers are embedded is transparent with respect to the radiation so that projection images of the fiducial markers are obtained by the image detector. For example, one of the six fiducial markers may be placed in the center of the cube or approximately in the center of the cube. From the center point of this central fiducial marker, a vector V extends to each of the center points of the other five fiducial markers. Based on prior knowledge about the constitution of the phantom, the coordinates of the vectors V are precisely known. The arrangement of the fiducials in the volume of the module is arbitrary to some extent, i.e., other phantoms of the same type with a different local distribution of the fiducial markers can be used alternatively. In addition, the number of fiducial markers within the phantom may be different.

Figure 3:
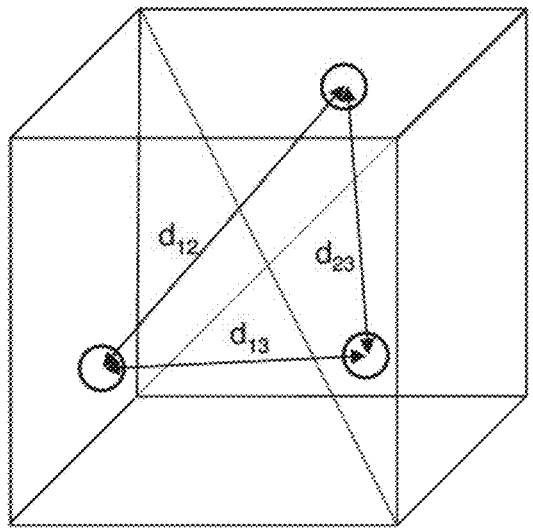
FIG. 3 shows schematically an exemplary embodiment of a calibration module in the form of a cube with three spherical fiducial markers.

FIG. 3 shows an exemplary embodiment of a calibration module M2 in the form of a cube. The three fiducial markers of radiation opaque material that are arranged within the cube of radiation transparent material are spherical fiducials (i.e., ball markers). Typically, none of the three fiducial markers is placed in the center of the cube. The known distances d between the center points of the fiducial markers are shown in the figure. The arrangement of the fiducials in the volume of the module is arbitrary to some extent, i.e., other calibration modules of the same type with a different local distribution of the fiducial markers can be used alternatively. In addition, the number of fiducial markers within the calibration module may be greater than three.

The shapes of the phantom shown in FIG. 2 and/or of the calibration module shown in FIG. 3 may differ in other exemplary embodiments. For example, the shape may be the shape of a cuboid or of a cylinder.

The coordinate system defined by the phantom M1 may be used as the coordinate system in which the geometrical information is determined. For example, all parameters, constants and coefficients that describe the geometrical information can be determined with respect to this coordinate system. For the assumption-free determination of the position of a characteristic point of the radiation source unit (such as the radiation origin point of the central axis of the radiation beam), only the phantom is required, provided that the pixel size of the projection images obtained by using the image detector is known. In other words, the calibration module M2 is not required for the determination of a single characteristic point of the radiation source unit. The same applies to the determination of the distance between the radiation source unit and the image detector and applies to the orientation of the image detector in space.

The calibration module (for example the module shown in FIG. 3) is used to determine the rotation angles and rotation axes of the radiation source unit and/or of a part of the radiation source unit. In particular, the rotation of the radiation source unit may be a rotation around the same rotation axis and with the same rotation angle as a gantry to which the radiation source unit is attached. A part of the radiation source unit that is rotatable around another rotation axis relative to the radiation source may be a collimator. The radiation source unit and (if applicable) the independently rotatable part of the radiation source unit is rotatable relative to the patient support. In practice, the position and orientation of the patient support is represented by the phantom that is attached to the patient support.

There is no need to describe an example of determining the position of the characteristic point of the radiation source unit in detail here, since corresponding methods are known from publications describing applications of the above-mentioned approach (e.g. W. Mao, L. Lee, L. Xing, "Development of a QA phantom and automated analysis tool for geometric quality assurance of on-board MV and kV X-ray imaging systems," Med. Phys. 35, 1497-1506 (2008); N. Robert, K. N. Watt, X. Wang, J. G. Mainprize, "The geometric calibration of cone-beam systems with arbitrary geometry," Phys Med Biol. 54, 7239-7261 (2009); On-Board Imager (OBI) Advanced Imaging Maintenance Manual, version B502203R01D, Varian Medical Systems, Inc., USA, April 2012, chapter 11, pp. 178-205). In the following, examples of determining the rotation angles and rotation axes will be described.

Because the central axis of radiation may unsteadily move during the rotation, for example as the result of flexing or sagging of the system under its own weight and/or aging of bearing mechanisms, the actual rotation axis and the actual rotation angle (from one rotational position to another rotational position) of the radiation source unit (in particular with respect to the rotation of the complete radiation source unit relative to the patient support or with respect to the rotation of the collimator relative to the patient support) depend on the rotational position. Therefore, the real rotational positions and the real orientation of the radiation source unit may differ from nominal positions and orientation. In other words, the rotation axis is not fixed in space while the rotation is performed.

As shown below, the use of a multi-fiducial calibration module attached to the radiation source unit allows for in particular assumption-free determination of the rotation axis as a function of the rotational position or of the rotation axes as functions of the rotational positions. In particular, an average rotation axis can be determined, such as for collimator rotation while there is no relative rotation of the patient table and the radiation source unit, or for another rotation axis. Furthermore, the position and/or orientation of the radiation axis and/or the radiation isocenter can be determined using the calibration module that is attached to the radiation source unit. From the geometrical information obtained with respect to the rotation of the radiation source unit, with respect to the rotation of the patient support and/or with respect to the rotation of a part of the radiation source unit, the mechanical isocenter can be determined. "Determination of an isocenter" in particular means that fluctuations of the position of the isocenter during rotation are considered and/or determined.

The following example of a method of determining geometrical information assumes that, for a plurality of rotational positions of the radiation source unit or of a part of the radiation source unit, the normal to the imaging plane of the image detector, the source to detector distance, the source position and the two-dimensional coordinate system (e.g., described by its coordinate axes $E_x$ and $E_y$, see FIG. 4) in the imaging plane have been determined and/or are known, in particular with respect to the coordinate system of the phantom, based on methods described in published articles (e.g., W. Mao, L. Lee, L. Xing, "Development of a QA phantom and automated analysis tool for geometric quality assurance of on-board MV and kV X-ray imaging systems," Med. Phys. 35, 1497-1506 (2008); N. Robert, K. N. Watt, X. Wang, J. G. Mainprize, "The geometric calibration of cone-beam systems with arbitrary geometry," Phys Med Biol. 54, 7239-7261 (2009); On-Board Imager (OBI) Advanced Imaging Maintenance Manual, version B502203R01D, Varian Medical Systems, Inc., USA, April 2012, chapter 11, pp. 178-205). In the following, the coordinate system of the phantom or of the patient support with respect to which the geometrical information is given and/or determined and which can be in particular the coordinate system of the phantom, will be referred to as "the global coordinate system."

Figure 4:
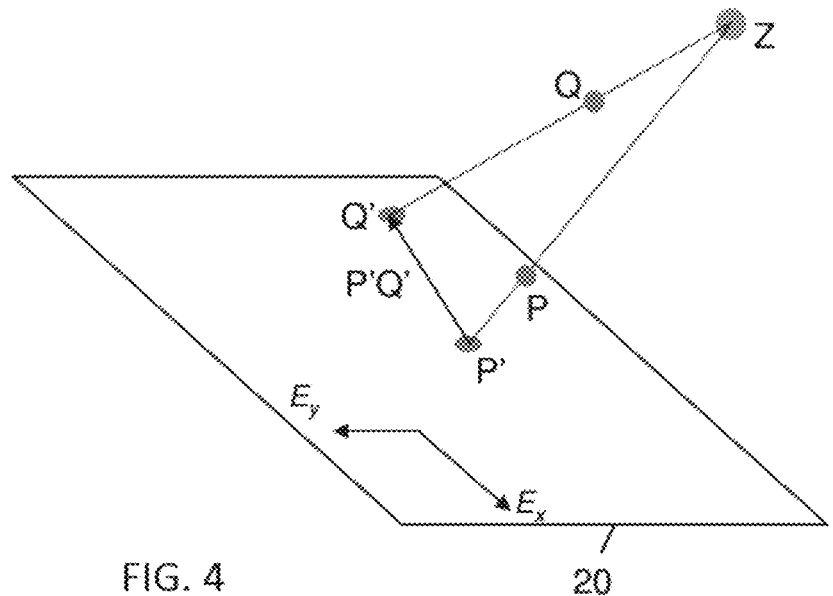
FIG. 4 shows a three-dimensional view of a projection of one fiducial marker of a phantom and of one fiducial marker of a calibration module from a source onto an image plane.

Using the geometrical information mentioned in the preceding paragraph, the coordinates of the projections of the fiducial markers of the phantom can be determined. FIG. 4 illustrates the geometrical situation for one fiducial marker of the phantom and one fiducial marker of the calibration module. Two projection lines from the source Z to the image plane are illustrated by straight lines. There is the characteristic position P of one fiducial marker of the phantom on one of the projection lines and there is the characteristic position Q of one fiducial marker of the calibration module on the other one of the projection lines. The positions of the corresponding projection points are denoted by P' and Q'. In addition, the vector starting at position P' and ending at position Q' is denoted by P'Q'.

The calibration module (in particular the calibration module of FIG. 1 or 3) is rigidly attached to the calibration source unit, for example as described above to the collimator. One task is to find the coordinates of the calibration module fiducials in the global coordinate system. Although these coordinates cannot be assessed directly, the global coordinates of their projections onto the image plane can be determined. For example, in FIG. 4, the global coordinates of position P are known, since all positions and their distances of the fiducial markers of the phantom are known. The global coordinates of the projection position P' of the position P can be determined. In addition, for a position Q of a fiducial marker within the calibration module, its projection position Q' in the image plane can be determined from the obtained image and the components of the P'Q' vector can be determined as well in the global coordinate system, as the vectors of the coordinate axes $E_x$ and $E_y$ of the image plane are known. Consequently, the components of the projected position Q' in the global coordinate system can be determined as well. Furthermore, it is known that the fiducial marker position Q lies somewhere on the projection line connecting the projection position Q' and the source position Z. Therefore, the global coordinates of both positions Q' and Z can be determined from the evaluation of the projection images of the fiducial markers of the phantom.

Figure 5:
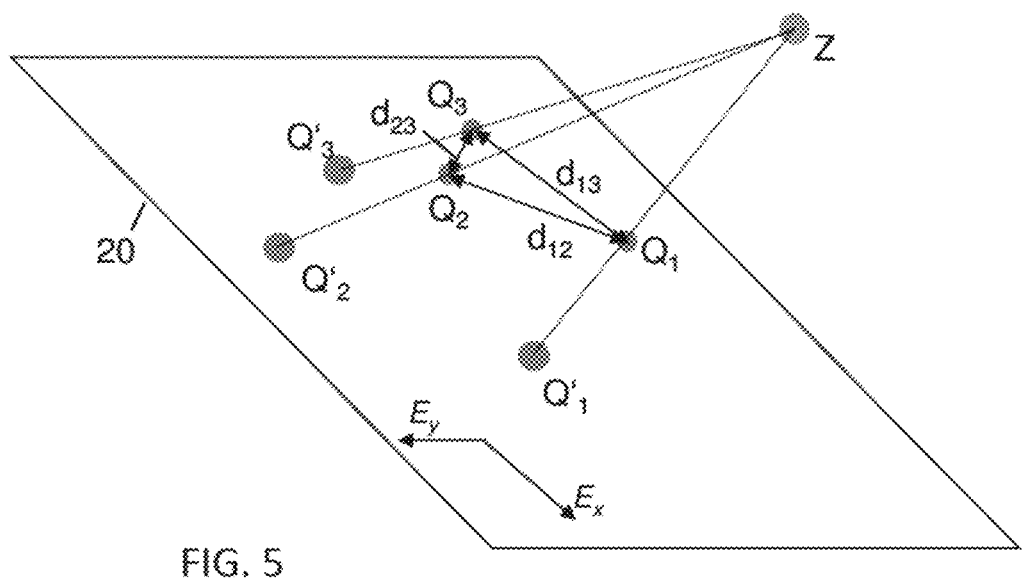
FIG. 5 shows a three-dimensional view of a projection of three fiducial markers of a calibration module from a source onto an image plane.

The calibration module includes at least three fiducial markers, corresponding to positions $Q_1$, $Q_2$, and $Q_3$ in FIG. 5. Their mutual distances $d_{12}$, $d_{13}$, and $d_{23}$ are also shown in FIG. 5. Therefore, the following equations (1) apply:

$$\forall i=1,2,3 \; \exists t_i \in (0,1) : Q_i = Z + t_i \overline{ZQ'_i}$$

$$\forall i=1,2,3; \; j=1,2,3; \; i \neq j \; |\overline{Q_iQ_j}| = d_{ij} \quad (1)$$

wherein ZQ' is the vector between the position Z of the source and the respective projection point position Q' in the image plane. In FIG. 5, the distances of the positions Q are denoted by d followed by the two indices of the respective two positions. According to the second line of equations (1), the distances of the positions Q are equal to the respective known distances d. However, it is typically not possible to find a position on each of the three projection lines for which the pairwise distances are exactly equal to the known distances d.

On the other hand, the first line of equations (1) provides three independent equations for three unknowns, namely the parameters $t_1$, $t_2$, and $t_3$, and these unknowns can be found for example by minimization of the following cost function G:

$$G(t_1, t_2, t_3) = \sum_{i,j=1,2,3; i \neq j} (|\overline{Q_iQ_j}| - d_{ij})^2 \quad (2)$$

To make the determination of the positions Q more robust with the respect to imperfect imaging, a calibration module having a larger number of fiducial markers can be used. In this case, the index variable assumes more than three values and the cost function G includes more than three terms in the summation defined on the right-hand side of the equation (2). In this case, the solution of the minimization problem defined in equation (2) delivers the global coordinates of the fiducial markers of the calibration module.

In the following, a method of determining the rotation angle and the rotation axis using images for two rotational positions of the radiation source unit will be described. In particular, the rotation may be caused by a rotation of the complete radiation source unit corresponding to the rotation of a gantry (if applicable) or the rotation may be caused by a rotation of a part of the radiation source unit, such as a collimator.

The rotation angle is denoted by θ and the rotation axis is represented by a vector $a=(a_x,a_y,a_z)$, $|a|=1$, passing through a point $P_0=(P_{0x},P_{0y},P_{0z})$. The position of a fiducial marker of the calibration module prior to rotation (i.e., at the first rotational position) is denoted by $X_0=(X_{0x},X_{0y},X_{0z})$ and after rotation (i.e., at the second rotational position) is denoted by $X_N=(X_{Nx},X_{Ny},X_{Nz})$. The coordinates of $X_N$ in the global coordinate system are given by equation (3):

$$\begin{pmatrix} X_{Nx} \\ X_{Ny} \\ X_{Nz} \\ 1 \end{pmatrix} = T(X_0) = \begin{pmatrix} 1 & 0 & 0 & P_{0x} \\ 0 & 1 & 0 & P_{0y} \\ 0 & 0 & 1 & P_{0z} \\ 0 & 0 & 0 & 1 \end{pmatrix} R \begin{pmatrix} 1 & 0 & 0 & -P_{0x} \\ 0 & 1 & 0 & -P_{0y} \\ 0 & 0 & 1 & -P_{0z} \\ 0 & 0 & 0 & 1 \end{pmatrix} \begin{pmatrix} X_{0x} \\ X_{0y} \\ X_{0z} \\ 1 \end{pmatrix} \quad (3)$$

$$R = \begin{pmatrix} c+a_x^2(1-c) & a_xa_y(1-c)-a_zs & a_xa_z(1-c)+a_ys & 0 \\ a_xa_y(1-c)+a_zs & c+a_y^2(1-c) & a_ya_z(1-c)-a_xs & 0 \\ a_xa_z(1-c)-a_ys & a_ya_z(1-c)+a_xs & c+a_z^2(1-c) & 0 \\ 0 & 0 & 0 & 1 \end{pmatrix}$$

where T is the rigid-body transformation corresponding to the movement of the complete radiation source unit or to the movement of a part of the radiation source unit, $c=\cos(\theta)$, $s=\sin(\theta)$ and R is the well-known axis-angle representation of the rotation matrix. Then, given a set $B=\{X_{0,i}, i=1 \ldots M\}$ of coordinates $X_{0,i}$ before rotation and a set $A=\{X_{N,i}, i=1 \ldots M\}$ of corresponding coordinates $X_{N,i}$ after rotation, the problem of determining the transformation matrix T can be formulated for example as a problem of minimizing the following cost function F(A,B,T):

$$F(A, B, T) = \sum_{i=1}^{M} \|X_{N,i} - T(X_{0,i})\|^2 \quad (4)$$

Consequently, from the analysis of the projections of fiducial markers of the calibration module, the actual rigid body movement of the radiation source unit or of part of the radiation source unit can be obtained. Then, the average rotation axis of either the complete radiation source unit (which may be equivalent to the rotation of a gantry) or of a part of the radiation source unit (e.g., a collimator) as well as the deviations from the average rotation axis can be derived with the methods described below.

In the following, an exemplary embodiment of a method of determining an average rotation axis for a range of rotational positions or for the whole range of rotational positions (360 degrees, one complete turnaround the rotation axis) is described. Again, the rotation axis may be the rotation axis of the complete radiation source unit or of a part of it, e.g., the collimator.

$U_i$ denotes the orientation of a momentary rotation axis of a rotation between two rotational positions. For each pair of rotational positions, the momentary rotation axis can be determined by performing the method described before. Of course, the orientation $U_i$ of the momentary rotation axis depends on both rotational positions. It is possible to determine the average orientation for a plurality of orientations $U_i$. The average orientation vector U can be found (e.g., using a least square method) by minimizing the errors $H_i$ of the orientations $U_i$ with the respect to the average orientation U being constrained to unit length (FIG. 6):

$$U = \min_{|U|=1} \arg \sum_i |H_i(U)|^2 = \min_{|U|=1} \arg \sum_i |U_i - (U_i \cdot U)U|^2, \quad (5)$$

Figure 6:
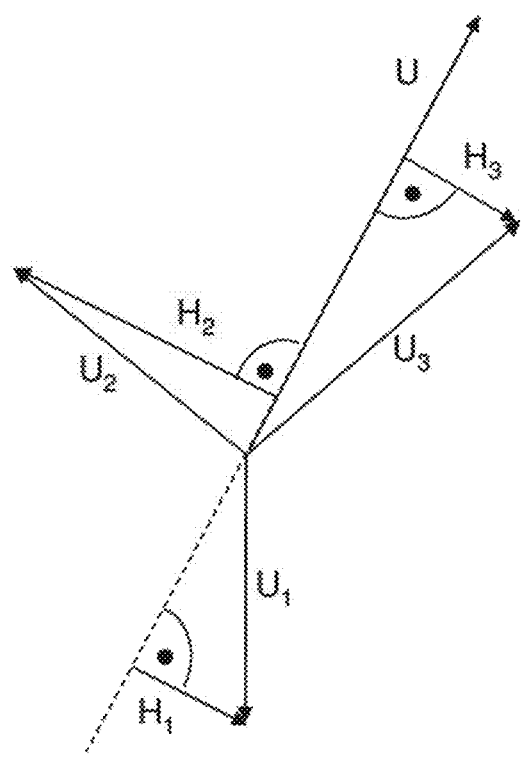
FIG. 6 shows a vector diagram with three momentary rotation axes, a mean orientation vector and the errors of the three momentary rotation axes that extend perpendicularly to the mean orientation vector.

In FIG. 6, an exemplary embodiment with three momentary rotation axes, i.e., with three orientations $U_i$ is shown. The lines which represent the errors $H_i$ of the three orientations $U_i$ extend perpendicularly to the straight line which is co-linear with the average orientation vector U.

It can be shown that the average orientation vector U is the principal vector corresponding to the maximal principal value of the covariance matrix C of the orientations $$C = \begin{pmatrix} \sum_i U_{ix}U_{ix} & \sum_i U_{ix}U_{iy} & \sum_i U_{ix}U_{iz} \\ \sum_i U_{iy}U_{ix} & \sum_i U_{iy}U_{iy} & \sum_i U_{iy}U_{iz} \\ \sum_i U_{iz}U_{ix} & \sum_i U_{iz}U_{iy} & \sum_i U_{iz}U_{iz} \end{pmatrix} \quad (6)$$

The principal values and principal directions of the covariance matrix C define a three-axis ellipsoid. The wobbling of the rotation axis is maximal for the principal direction corresponding to the largest principal value of C. The variances of the data with the respect to the principal directions are thus useful information for the quality control in radiotherapy/radiosurgery. In particular, the principal values and principal directions of the covariance matrix C, in particular the largest principal value, represent(s) measures of the undesired variation (movement) of the rotation axis.

In the following, an exemplary embodiment of a method of determining the coordinates of an isocenter (i.e., its position in particular in the global coordinate system) is described. Momentary rotation axes and rotation angles of radiation axes, which are for example determined as described above, can be used as geometrical input information of the determination method. Different isocenters, in particular the isocenters mentioned above, can be determined by the method. Each isocenter can be determined by using a minimization procedure, in particular a least-squares method.

Figure 7:
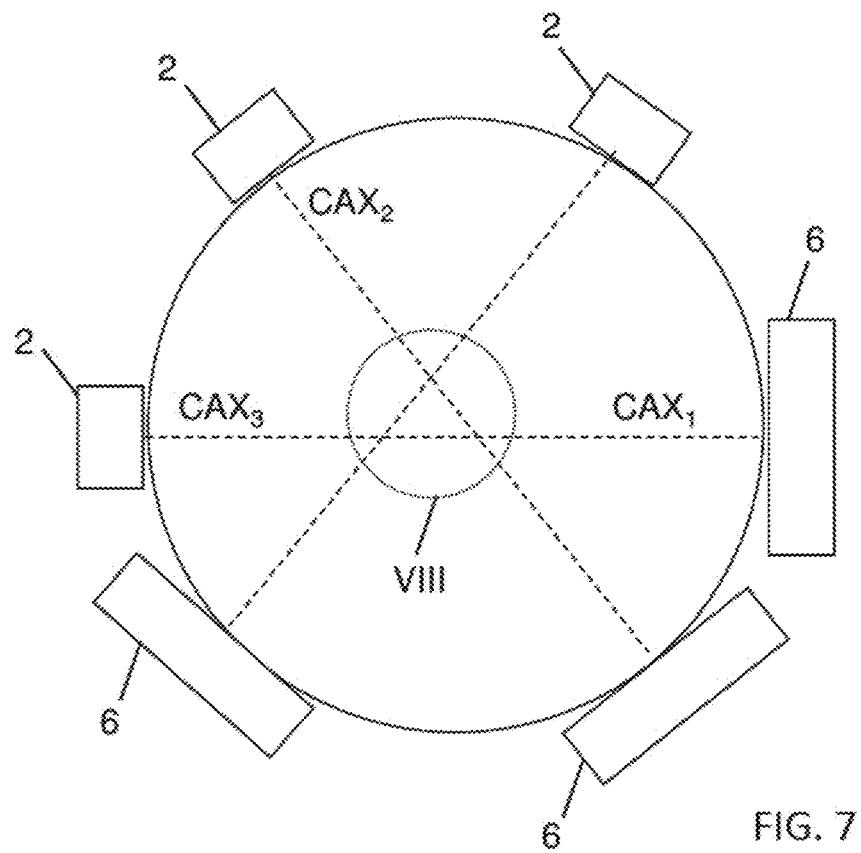
FIG. 7 shows the radiation axes, i.e., the central axes of the radiation beam between the source and the image detector, for three rotational positions.
Figure 8:
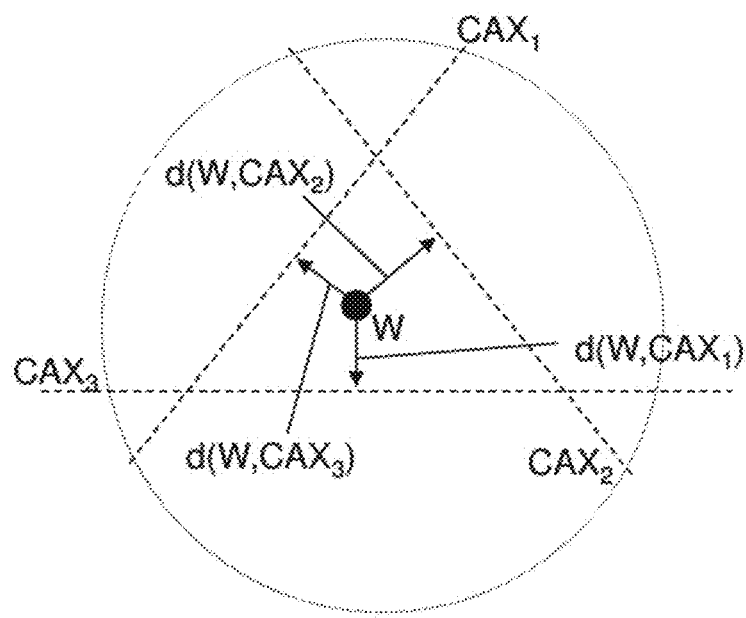
FIG. 8 shows an enlarged view of a target area including the isocenter of the arrangement shown in FIG. 7.

In the exemplary embodiment described here and illustrated in FIG. 7, the mechanical isocenter with respect to the rotation of the radiation source unit and the image detector around their rotation axis is determined. However, the isocenter with respect to any other rotation axis or combination of rotation axes can be determined in a similar manner. As shown in FIG. 7, the radiation axes (center beam propagation lines which may also be the rotation axes of the collimator) are denoted by $CAX_i$, wherein i denotes the index of the respective radiation axis. For example, if a number of N radiation axes is considered, i assumes the integer values from 1 to N. The positions and orientations of the radiation axes $CAX_i$ have been determined before. The position IS of the isocenter can be determined by solving the following minimization problem:

$$IS = \min_W \arg \sum_{i=1}^N d^2(W, CAX_i), \quad (7)$$

i.e., minimizing the sum of the squares of the distances d of the radiation axes $CAX_i$ to positions W, especially positions within a target area. The target area may be defined as an area of positions, which area most likely contains or for plausibility reasons contains the isocenter position. FIG. 7 and FIG. 8 show an exemplary embodiment for N=3 radiation axes. Each radiation axis $CAX_i$ extends from the radiation source unit 2 to the image detector 6 for the respective rotational position. FIG. 8 shows an enlarged view of the central area VIII of FIG. 7. In the exemplary embodiment, the target area is defined by the triangle, and the edges of which are defined by the radiation axes $CAX_i$. In case of more radiation axes $CAX_i$, the target typically has a different shape. In FIG. 8, d(W, $CAX_i$) denote the distances of an exemplary position W within the target area to the radiation axes.

More generally speaking, if an isocenter position with respect to one rotational axis or more than one rotational axis is to be determined by the minimization procedure, the target area is a volume in space, rather than an area within a plane. This especially applies to the isocenter with respect to two rotational axes. However, this also applies to the exemplary embodiments shown in FIG. 7 and FIG. 8 if the three rotational axes do not intersect each other pairwise. However, in any case, the radiation axis for each combination of rotational positions with respect to the plurality of rotational axes can be determined and the position can be identified for which the sum of the distances or of the square of the distance to the radiation axes is minimal.

In the following, it is shown that the problem defined by equation (7) can be solved analytically, because it is quadratic in the coordinates $W_x$, $W_y$, and $W_z$ of an arbitrary point W within the target area. As each radiation axis $CAX_i$ can be represented as a straight line in the three-dimensional space, we have:

$$CAX_i : \{ \vec{x} : \vec{x} = \vec{a_i} t + \vec{v}_{0,i}, t \in \mathfrak{R} \}$$

$$\vec{a_i} = (a_{x,i}, a_{y,i}, a_{z,i})$$

$$|a_i| = 1$$

$$\vec{v}_{0,i} = (x_{0,i}, y_{0,i}, z_{0,i}) \quad (8)$$

wherein $t \in \mathfrak{R}$ denotes that t is a real number, a denotes a vector having a unit length and extending in the direction of the radiation axis and $v_{0,i}$ denotes a point in space located where the radiation axis starts at the radiation source.

By taking the derivatives of the cost function $$K(V) = \sum_{i=1}^N d^2(W, CAX_i)$$

on the right-hand side of equation (7) with respect to the coordinates of the positions W, it can be shown that the least-squares estimates is$_x$, is$_y$, and is$_z$ of the coordinates IS$_x$, IS$_y$, and IS$_z$ of the isocenter IS are the solution of the following set of three linear equations:

$$\begin{pmatrix} N - \sum_{i=1}^{N} a_{x,i}a_{x,i} & -\sum_{i=1}^{N} a_{y,i}a_{x,i} & -\sum_{i=1}^{N} a_{z,i}a_{x,i} \\ -\sum_{i=1}^{N} a_{y,i}a_{x,i} & N - \sum_{i=1}^{N} a_{y,i}a_{y,i} & -\sum_{i=1}^{N} a_{z,i}a_{y,i} \\ -\sum_{i=1}^{N} a_{z,i}a_{x,i} & -\sum_{i=1}^{N} a_{z,i}a_{y,i} & N - \sum_{i=1}^{N} a_{z,i}a_{z,i} \end{pmatrix} \begin{pmatrix} is_x \\ is_y \\ is_z \end{pmatrix} = \qquad (9)$$

$$\begin{pmatrix} \sum_{i=1}^{N} (x_{0,i} - a_{x,i}a_{x,i}x_{0,i} - a_{y,i}a_{x,i}y_{0,i} - a_{z,i}a_{x,i}z_{0,i}) \\ \sum_{i=1}^{N} (y_{0,i} - a_{y,i}a_{x,i}x_{0,i} - a_{y,i}a_{y,i}y_{0,i} - a_{z,i}a_{y,i}z_{0,i}) \\ \sum_{i=1}^{N} (z_{0,i} - a_{z,i}a_{x,i}x_{0,i} - a_{y,i}a_{z,i}y_{0,i} - a_{z,i}a_{z,i}z_{0,i}) \end{pmatrix}$$

There are at least two reasons for uncertainties in the estimation of the position of the isocenter. The first reason refers to the random measurement errors related to the estimation of the components of the vector $a_i$ and of the point $v_{0,i}$ and to the actual selection of the orientations of the rotation axis/axes. The second reason are the numerical errors of the minimization procedure performed in order to determine the vector $a_i$ and the point $v_{0,i}$. The uncertainties related to the latter reason are the direct consequence of the fact that the results of a minimization procedure may depend on its initialization (in particular defined by a set of start values) and thus are not guaranteed to be Gaussian distributed. Consequently, it is typical to repeat the minimization procedure starting with different initializations in order to estimate and/or to reduce these uncertainties.

Figure 9:
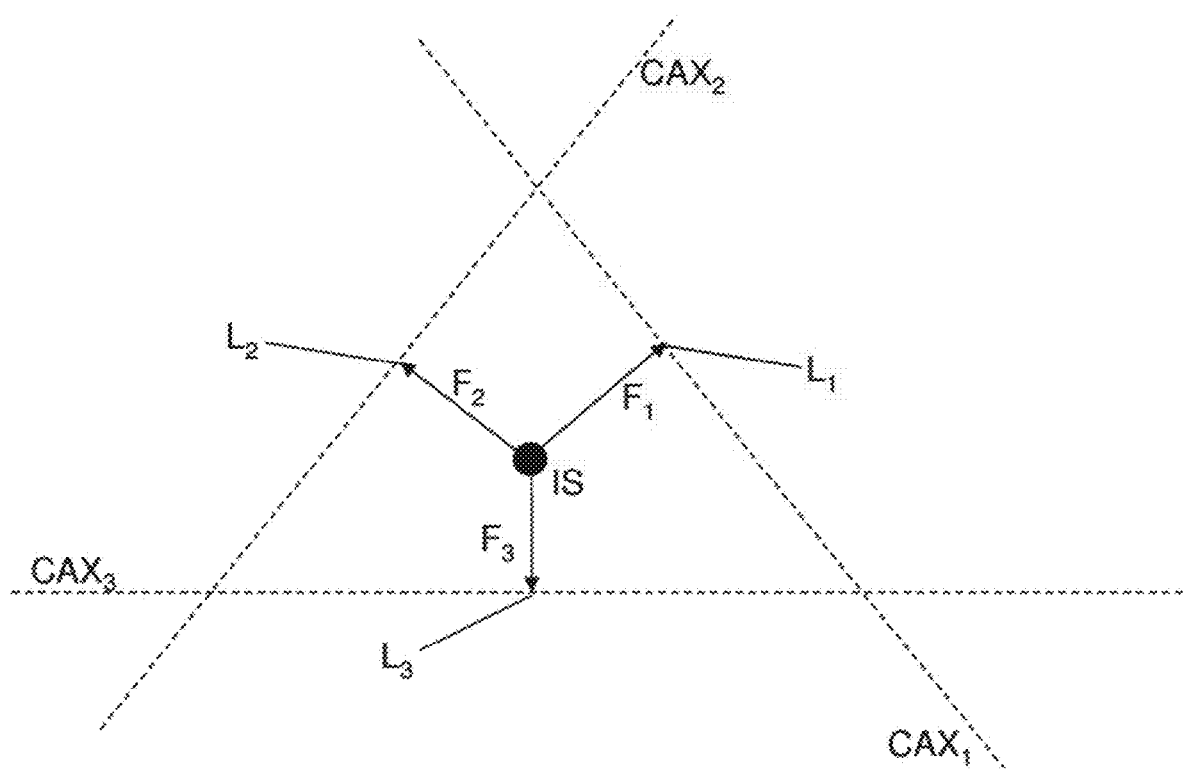
FIG. 9 shows an example of an arrangement comprising three radiation axes and a determined isocenter, wherein projections of the isocenter onto the radiation axes are illustrated, and FIG. 10 schematically shows a projection of three fiducial marker lines.

When the position of the isocenter IS and the radiation axes $CAX_i$ have been determined, the wobbling of the radiation axes around the isocenter can be assessed. In particular, the isocenter IS can be projected onto each radiation axis $CAX_i$ resulting in a plurality of projection points $L_i$ (FIG. 9). Then, the vectors $F_i$ pointing from the isocenter IS to the respective projection point $L_i$ can be calculated: $F_i=L_i-IS$. Typically, the average orientation vector F for all vectors $F_i$ is calculated as a characteristic of the wobbling. The average orientation vector F can be determined by using a least squares method, e.g., analogue to the least squares method mentioned in connection with FIG. 6 above. FIG. 9 illustrates the projection for an arrangement of three radiation axes $CAX_i$ similar to the arrangement shown in FIG. 7 and FIG. 8. The projection vectors $F_i$ extend perpendicularly to the respective radiation axis.

In order to reliably determine the position of an isocenter and to quantitatively characterize wobbling, the radiation axis $CAX_i$ is to be determined for a plurality of rotational positions with respect to the corresponding rotation axis/axes (e.g., the rotation axis of a gantry and/or of a collimator).

Further geometrical information can be determined using the calibration module that is attached to the radiation source unit. In particular the position of elements (the so-called jaws) of a collimator that is part of the radiation source unit, the size of the radiation field generated by the radiation source unit, movements of the treatment table and/or the natural coordinate system related to the device can be determined. Using geometrical information related to at least one isocenter of the arrangement, geometrical information about other devices of the arrangement can be determined, in particular about room lasers, telemeters, or a light simulation field.

In the following, a second exemplary embodiment for determining the position and/or orientation of the calibration module, and thereby of the radiation source unit, or the respective rotation angle is described.

According to the second exemplary embodiment, there is a plurality of n points of the calibration module which are defined by fiducial markers (e.g., by point markers or by the end points of line markers), wherein n is an integer. A principal difference between the second exemplary embodiment and the first exemplary embodiment described before with reference to FIG. 5, is the fact that the n points of the calibration module and their pairwise distances are fixed, but there is no need to know the coordinates of the points and the distances explicitly.

These n fiducials points are denoted by $Q_1, Q_2, \ldots,$ and $Q_n$. Now, two different rotational positions of the radiation source unit relative to the patient support or relative to any other part of the arrangement are considered, namely an initial position O and a target position N. In the same manner as in the case of the first example, the global coordinates of the projection points $Q'_O$ of the fiducial points $Q_O$ for the initial position O and of the projection points $Q'_N$ of the fiducial points $Q_N$ for the target position N can be determined. For the initial position O, each of the fiducial points $Q_O$ is located somewhere along the straight line connecting its projection point $Q'_O$ and the initial source position $Z_O$. Similarly, for the target position N, each of the fiducial points $Q_N$ is located somewhere along the straight line connecting its projection point $Q'_N$ and the target source position $Z_N$. The global coordinates of all these points can be determined from an analysis of projection images of the phantom. Since the distances between the fiducials points Q remain constant (although they may be unknown) while rotating, then we have the following conditions:

$$\forall i=1,\ldots,n \ \forall t_{i,N}:Q_{i,N}=Q'_{i,N}+t_{i,N}\sqrt{Q'_{i,N}Z_N}$$

$$\forall i=1,\ldots,n \ \forall t_{i,O}:Q_{i,O}=Q'_{i,O}+t_{i,O}\sqrt{Q'_{i,O}Z_O}$$

$$\forall i=1,\ldots,n; j=1,\ldots,n; i\neq j |\sqrt{Q_{i,N}Q_{j,N}}|=|\sqrt{Q_{i,O}Q_{j,O}}| \qquad (10)$$

Herein, $t_{i,O}$ and $t_{i,N}$ are parameters describing the position of one of the fiducial points Q on the respective straight line connecting the projection point Q' with the source position Z. Therefore, the set of equations (10) includes $n(n-1)/2$ independent equations for the 2n parameters t. In order to determine the fiducial points for the initial rotational position and for the target rotational position in the three-dimensional global coordinate system, n=5 fiducial points Q are required. When these ten fiducial points (five fiducial points of the initial rotational position and five fiducial points of the target rotational position) have been determined, the corresponding transformation that transforms the five fiducial points of the initial rotational position to the five fiducial points of the target rotational position can be calculated and the corresponding rotation angle can be determined.

In the following, a third example of determining the position and/or orientation of the calibration module, and thereby of the radiation source unit, or of the respective rotation angle is described. In this example, straight linear markers and their angles are used instead of fiducial points. When a rigid body like of the radiation source unit together with the calibration module rotates, the angles formed by any three different points remain unchanged. However, the projections of these angles depend on the rotational position.

Figure 10:
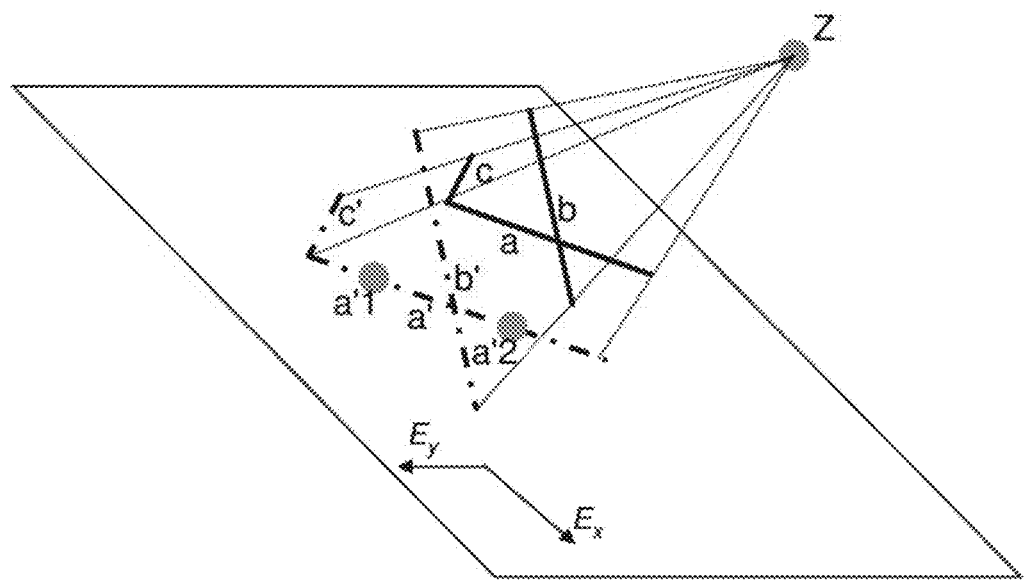

FIG. 10 schematically shows a projection similar to the projection shown in FIG. 5. While FIG. 5 shows the projection of three fiducial points of a calibration module onto the image plane of the detector, FIG. 10 shows the projection of three fiducial marker lines a, b, and c. The corresponding projected lines are denoted by a', b', and c'. In addition, two points a'1 and a'2 are shown on the projected line a'.

The angles between each pair in the set of the three lines a, b, and c are known. For each of the rotational positions of the radiation source unit the lines a, b, and c are projected onto lines a', b', and c', respectively (FIG. 10) and the respective projection image is generated. The coordinates, in particular the positions and orientations, of the projected lines a', b', and c' can be determined in each of the projection images, e.g., by applying an image analysis algorithm (for example using a Hough transform) and then—based on an analysis of the projections of structures of the phantom—the 3-dimensional global coordinates of arbitrary two points (e.g., a'1 and a'2 in line a) within each projected line a', b', and c' are determined. Based on the global coordinates of these points as well as the global coordinates of the source Z, for each of the projected lines a', b', and c' the equation of the plane unambiguously defined by the two points and by the source Z can be determined. For example, for line a, the normal line $n_a$ onto the plane is given by the cross product of the vector connecting the point a'1 and the source Z and of the vector connecting the second point a'2 and the source Z:

$$n_a = (a'_1 - Z) \times (a'_2 - Z) \tag{11}$$

Thus, the plane $P_a$ that includes the projected line a' and the source Z is described by:

$$P_a = \{X \in R^3 : n_a \cdot (X - Z) = 0\} \tag{12}$$

wherein X is any point in the plane, i.e., X can assume each set of coordinates of points in the plane. Analogous equations for the plane $P_b$ with respect to the second line b and its projected line b' as well as for the plane $P_c$ with respect to the third line c and its projected line c' can be set for the other two segments. In these two analogous equations, the normal lines $n_b$ and $n_c$ are used that corresponds to the normal line $n_a$.

Now, let A be a unit length vector within line a, B a unit length vector within line b, and C a unit length vector within line c, ab be an angle of known size between lines a and b, bc be an angle of known size between lines b and c and ca be an angle of known size between lines c and a. Then, the following set of nine equations for nine unknown components of the vectors A, B, and C can be set-up:

$$A \cdot n_a = 0$$

$$B \cdot n_b = 0$$

$$C \cdot n_c = 0$$

$$\|A\| = 1$$

$$\|B\| = 1$$

$$\|C\| = 1$$

$$A \cdot B = \cos(ab)$$

$$A \cdot C = \cos(ac)$$

$$B \cdot C = \cos(bc) \tag{13}$$

From the set of equations (13), the vector components of A, B, and C can be determined in particular for an initial rotational position and a target rotational position of the radiation source unit relative to any other part of the arrangement. Furthermore, the transformation (e.g., the rotation axis and the rotation angle) between the initial rotational position and the target rotational position can be determined from the vector components of the vectors A, B, and C in the same manner as in the case of the first and the second example.

It is understood that the foregoing description is that of the exemplary embodiments of the invention and that various changes and modifications may be made thereto without departing from the spirit and scope of the invention as defined in the appended claims.

LIST OF REFERENCE SIGNS a, b, c straight lines (fiducial marker lines)
a', b', c' projections of straight lines
a'1 first point on projection line a'
a'2 second point on projection line a'
d distance
$e_x, e_y, e_z$ coordinate axes of coordinate system of phantom
$E_x, E_y$ coordinate axes of coordinate system of image plane
$F_i$ projection vector
IS position of isocenter
$H_i$ error of the momentary rotation axes
$L_i$ projection point
M1 phantom
M2 calibration module
M3 detector module
P position of fiducial marker of phantom
P' projection of fiducial marker of phantom onto image plane
Q position of fiducial marker of calibration module
Q' projection of fiducial marker of calibration source onto image plane
P'Q' vector from P' to Q'
U average orientation vector
$U_i$ momentary rotation axis
V vector from fiducial marker to another fiducial marker within phantom
Z position of source
1 radiation treatment arrangement
2 radiation source unit
3 radiation source
4 collimator
5 gantry
6 image detector
7 lines indicating narrowed radiation beam
8 diverging lines indicating cone shaped radiation beam
10 patient support
11 pillar
12 first fiducial marker
13 second fiducial marker
14 third fiducial marker
15 detector support
16 first rotation axis
17 second rotation axis
18 arrangement of fiducial markers (within module M1)
20 Image plane of detector

What is claimed is:
1. A method for determining geometrical information about a medical treatment arrangement including a rotatable treatment radiation source unit, the method comprising:
attaching a phantom to a patient support of the medical treatment arrangement;

attaching a calibration module to the rotatable treatment radiation source unit to permit the calibration module to rotate together with the rotatable treatment radiation source unit when the rotatable treatment radiation source unit is rotated;

obtaining for each rotational position of a plurality of rotational positions of the rotatable treatment radiation source unit, at least one projection image of the phantom and of the calibration module by an image detector of the medical treatment arrangement, while at least a part of the calibration module is positioned in a radiation propagation zone between the rotatable treatment radiation source unit and the image detector;

evaluating the at least one projection image obtained for each rotational position of the plurality of rotational positions with respect to coordinates of the calibration module in a coordinate system of the phantom, thereby obtaining an evaluation result; and determining geometrical information about the medical treatment arrangement from the evaluation result.

2. The method of claim 1, further comprising:

obtaining for each rotational position of at least a first rotational position and a second rotational position of the rotatable treatment radiation source unit, at least one projection image of the phantom and of the calibration module by the image detector comprises obtaining at least a first projection image corresponding to the first rotational position and a second projection image corresponding to the second rotational position; and evaluating at least the first projection image and the second projection image with respect to coordinates of the calibration module, thereby determining positions of the calibration module in the coordinate system of the phantom for each rotational position of at least the first rotational position and the second rotational position.

3. The method of claim 2, further comprising:

determining from the positions of the calibration module in the coordinate system of the phantom, determined for each rotational position of the first rotational position and the second rotational position, at least one of:

an angle of rotation of the rotatable treatment radiation source unit or of a part of the rotatable treatment radiation source unit between the first rotational position and the second rotational position, an orientation of a rotation axis around which the rotatable treatment radiation source unit or a part of the rotatable treatment radiation source unit has rotated between the first rotational position and the second rotational position, and a straight linear shift which the rotatable treatment radiation source unit or a part of the rotatable treatment radiation source unit has performed between the first rotational position and the second rotational position.

4. The method of claim 1, further comprising:

determining an orientation of an average rotation axis of the medical treatment arrangement from orientations of rotation axes determined for a plurality of rotation axes around which the rotatable treatment radiation source unit or a part of the rotatable treatment radiation source unit has rotated.

5. The method of claim 1, further comprising:

determining positions and orientations of a radiation axis of radiation from the rotatable treatment radiation source unit to the image detector for the plurality of rotational positions of the medical treatment arrangement with respect to at least one rotation axis; and determining an isocenter of the medical treatment arrangement with respect to the at least one rotation axis from the determined positions and orientations of the radiation axis.

6. The method of claim 1, wherein:

the calibration module includes a set of fiducial markers, and the method further comprises:

obtaining the at least one projection image of the phantom and of the calibration module for each rotational position of the plurality of rotational positions of the rotatable treatment radiation source unit by the image detector of the medical treatment arrangement, while the set of fiducial markers of the calibration module is positioned in the radiation propagation zone between the rotatable treatment radiation source unit and the image detector, and evaluating the at least one projection image obtained for each rotational position of the plurality of rotational positions with respect to coordinates of the set of fiducial markers in the coordinate system of the phantom, thereby obtaining the evaluation result.

7. A medical treatment arrangement comprising:

a rotatable treatment radiation source unit;

a patient support;

an image detector arranged to receive a radiation field that has been emitted by the rotatable treatment radiation source unit and that has interacted with any object in between the rotatable treatment radiation source unit and the image detector, the image detector being configured to produce projection images corresponding to the radiation field according to a result of interaction with at least one object;

a phantom attached to the patient support; and a calibration module attached to the rotatable treatment radiation source unit to permit the calibration module to rotate together with the rotatable treatment radiation source unit when the rotatable treatment radiation source unit is rotated.

8. The medical treatment arrangement of claim 7, further comprising:

a data storage including projection images generated by the image detector and configured to receive projection images of the phantom and of the calibration module obtained by the image detector for each rotational position of a plurality of rotational positions of the rotatable treatment radiation source unit;

an evaluation device connected to at least one of the image detector and the data storage while at least a part of the calibration module is positioned in a radiation propagation zone between the rotatable treatment radiation source unit and the image detector, and configured to evaluate the projection images with respect to coordinates of the calibration module in a coordinate system of the phantom, thereby obtaining an evaluation result; and a determination device being at least one of connected to the evaluation device or part of a common unit with the evaluation device, and configured to determine geometrical information about the medical treatment arrangement from the evaluation result.

9. The medical treatment arrangement of claim 8, wherein the evaluation device is configured to evaluate at least a first projection image corresponding to a first rotational position and a second projection image corresponding to a second rotational position with respect to coordinates of the calibration module, thereby determining positions of the calibration module in the coordinate system of the phantom for each rotational position of at least the first rotational position and the second rotational position.

10. The medical treatment arrangement of claim 9, wherein the determination device is configured to determine, from the positions of the calibration module in the coordinate system of the phantom determined by the evaluation device for each rotational position of the first rotational position and the second rotational position, and least one of:
  an angle of rotation of the rotatable treatment radiation source unit or of a part of the rotatable treatment radiation source unit between the first rotational position and the second rotational position,
  an orientation of a rotation axis around which the rotatable treatment radiation source unit or a part of the rotatable treatment radiation source unit has rotated between the first rotational position and the second rotational position, and
  a straight linear shift which the rotatable treatment radiation source unit or a part of the rotatable treatment radiation source unit has performed between the first rotational position and the second rotational position.

11. The medical treatment arrangement of claim 8, wherein the determination device is configured to determine an orientation of an average rotation axis of the medical treatment arrangement from orientations of rotation axes determined for a plurality of rotation axes around which at least one of the rotatable treatment radiation source unit or a part of the rotatable treatment radiation source unit has rotated.

12. The medical treatment arrangement of claim 8, wherein the determination device is configured to determine:
  positions and orientations of a radiation axis of radiation from the rotatable treatment radiation source unit to the image detector for the plurality of rotational positions of the medical treatment arrangement with respect to at least one rotation axis, and
  an isocenter of the medical treatment arrangement with respect to the at least one rotation axis from the determined positions and orientations of the radiation axis.

13. The medical treatment arrangement of claim 7, wherein the calibration module comprises a set of fiducial markers.

14. The medical treatment arrangement of claim 13, wherein the evaluation device is configured to:
  receive the projection images of the phantom and of the calibration module obtained by the image detector for each rotational position of a plurality of rotational positions of the rotatable treatment radiation source unit, while the set of fiducial markers of the calibration module is positioned in a radiation propagation zone between the rotatable treatment radiation source unit and the image detector, and
  to evaluate the projection images with respect to coordinates of the set of fiducial markers in a coordinate system of the phantom, thereby obtaining an evaluation result.

15. The medical treatment arrangement of claim 14, wherein the evaluation device is configured to evaluate at least a first projection image and a second projection image with respect to the coordinates of the set of fiducial markers of the calibration module, thereby determining positions of the set of fiducial markers in the coordinate system of the phantom for each rotational position of at least the first rotational position and the second rotational position.

16. The medical treatment arrangement of claim 15, wherein the determination device is configured to determine from the positions of the set of fiducial markers in the coordinate system of the phantom determined by the evaluation device for each rotational position of the first rotational position and the second rotational position at least one of:
  an angle of rotation of the rotatable treatment radiation source unit or of a part of the rotatable treatment radiation source unit between the first rotational position and the second rotational position,
  an orientation of a rotation axis around which the rotatable treatment radiation source unit or the part of the rotatable treatment radiation source unit has rotated between the first rotational position and the second rotational position, and
  a straight linear shift which the rotatable treatment radiation source unit or a part of the rotatable treatment radiation source unit has performed between the first rotational position and the second rotational position.

* * * * *